(12) United States Patent
Werner et al.

(10) Patent No.: US 9,110,002 B2
(45) Date of Patent: *Aug. 18, 2015

(54) SENSOR DEVICE

(75) Inventors: Wolfgang Werner, Heide (DE); Joachim Aurich, Welmbuttel (DE); Sascha Werth, Rendsburg (DE)

(73) Assignee: VISHAY BCCOMPONENTS BEYSCHLAG GMBH, Heide (DE)

( * ) Notice: Subject to any disclaimer, the term of this patent is extended or adjusted under 35 U.S.C. 154(b) by 27 days.

This patent is subject to a terminal disclaimer.

(21) Appl. No.: 13/549,930

(22) Filed: Jul. 16, 2012

(65) Prior Publication Data

US 2013/0039380 A1    Feb. 14, 2013

Related U.S. Application Data

(63) Continuation of application No. 12/514,555, filed as application No. PCT/EP2007/009505 on Nov. 2, 2007, now Pat. No. 8,220,988.

(30) Foreign Application Priority Data

Nov. 13, 2006    (DE) .................. 10 2006 053 689

(51) Int. Cl.
    *G01N 25/68*    (2006.01)
    *G01N 27/12*    (2006.01)
    *G01N 27/22*    (2006.01)

(52) U.S. Cl.
    CPC ......... *G01N 27/121* (2013.01); *Y10T 29/49124* (2015.01); *Y10T 29/49155* (2015.01)

(58) Field of Classification Search
    USPC ...................... 374/27, 28; 361/286
    See application file for complete search history.

(56) References Cited

U.S. PATENT DOCUMENTS

| 3,552,186 | A | * | 1/1971 | Sproul ........................... 374/21 |
| 4,453,397 | A |   | 6/1984 | Ohta et al. |
| 4,677,416 | A |   | 6/1987 | Nishimoto et al. |
| 4,731,257 | A | * | 3/1988 | Uchikawa ..................... 427/122 |
| 4,794,323 | A | * | 12/1988 | Zhou et al. .................. 324/71.5 |
| 4,948,263 | A | * | 8/1990 | Herrmann et al. ............. 374/28 |

(Continued)

FOREIGN PATENT DOCUMENTS

| DE | 3720189 C1 | 12/1988 |
| DE | 19606272 A1 | 8/1997 |

(Continued)

OTHER PUBLICATIONS

Vaivars G. et al. "Influence of thin film coatings on the gas sensitivity properties of narrow laser cut gap in IN2O3 on glass substrate" Sensors and Actuators B, Elsevier Sequoia, S.A., Lausanne, CH, Bd. 33, Nr.1, Jul. 1996, Seiten 173-177, XP004013064, ISSN: 0925-4005.

(Continued)

*Primary Examiner* — Mirellys Jagan
(74) *Attorney, Agent, or Firm* — Volpe and Koenig, P.C.

(57) ABSTRACT

A sensor device is provided for detecting thawing on surfaces with interdigital electrodes formed in a resistance layer which is formed on a substrate. In order to develop the sensor device further so that the measuring speed of the sensor device is further increased, the disclosure proposes that the interdigital electrodes and recesses between the interdigital electrodes have a moisture-sensitive hydrophilic surface through condensation cores applied to it.

21 Claims, 2 Drawing Sheets

(56) References Cited

U.S. PATENT DOCUMENTS

| | | | |
|---|---|---|---|
| 5,022,045 A * | 6/1991 | Elliott | 374/20 |
| 5,136,274 A * | 8/1992 | Shimomura et al. | 338/35 |
| 5,739,430 A * | 4/1998 | Berberich | 73/335.05 |
| 6,428,717 B1 * | 8/2002 | Sakai et al. | 216/83 |
| 6,614,241 B2 | 9/2003 | Schmitt et al. | |
| 6,787,047 B1 * | 9/2004 | Hahn et al. | 216/2 |
| 7,114,848 B2 | 10/2006 | Kaneko | |
| 2002/0048306 A1 * | 4/2002 | Sauvant et al. | 374/21 |
| 2003/0179805 A1 * | 9/2003 | Hamamoto et al. | 374/16 |
| 2010/0147070 A1 * | 6/2010 | Jun et al. | 73/335.05 |
| 2014/0007937 A1 * | 1/2014 | Maeda | 136/256 |
| 2014/0192836 A1 * | 7/2014 | Neilson | 374/28 |

FOREIGN PATENT DOCUMENTS

| | | |
|---|---|---|
| DE | 19708053 A1 | 9/1998 |
| DE | 10015430 C1 | 5/2001 |
| DE | 10114230 A1 | 10/2001 |
| WO | 9838499 A1 | 9/1998 |

OTHER PUBLICATIONS

Kleperis J et al."Gas-sensitive gap formation by laser ablation in IN2O3 layer: Application as humidity sensor" Sensors and Actuators B, Elsevier Sequoia, S.A., Lausanne, CH, Bd. 28, Nr. 2, Aug. 1995 Seiten 135-138, XP004001448, ISSN: 0925-4005.

* cited by examiner

SENSOR DEVICE

CROSS REFERENCE TO RELATED APPLICATIONS

This application is a continuation of U.S. patent application Ser. No. 12/514,555, filed May 12, 2009, issuing as U.S. Pat. No. 8,220,988 on Jul. 17, 2012, which is a §371 filing of International Patent Application No. PCT/EP2007/009505, filed Nov. 2, 2007, which claims foreign priority to German Patent Application No. 10 2006 053 689.4, filed Nov. 13, 2006, which are incorporated by reference as if fully set forth herein.

FIELD OF INVENTION

The invention relates to a sensor device for detecting thawing on surfaces with interdigital electrodes formed in a resistance layer, which electrodes are formed on a substrate. The invention also relates to a method for producing a sensor device provided with a substrate.

BACKGROUND

Sensor devices of the type already mentioned are known from the state of the art and are familiar to the person skilled in the art.

In EP 1 021 704 B1, a sensor device is disclosed in which a metal coating is applied to a substrate layer. The metal coating is in turn present in the form of interdigital electrodes which form a capacitor, a temperature-dependent resistance, which is at the same time used as a temperature sensor and heating element, being integrated in the capacitor. Moreover, a passivation layer is applied to the metal coating. The passivation layer consists of two layers, namely a lower hydrophobic layer and a hydrophilic layer arranged on top of it. The hydrophilic layer is in turn provided with condensation cores, thus ensuring that a detectable water film, which generates a signal that can be evaluated, is formed when the sensor device cools down by only a few degrees Kelvin before attaining the dew point. The upper and lower layers are, in this case, applied directly to the capacitor formed by the interdigital electrodes. The protective layers may be polymer layers.

A further sensor device of the type already mentioned is disclosed in DE 37 20 189 C1. DE 37 20 189 C1 describes a dew point sensor for a dew point meter for measuring the water vapour dew point in gases with a sensor surface exposed to the gas to be measured, on which surface water vapour condenses when it cools to the dew point temperature, and with two interdigital electrodes installed on the sensor surface with electrode sections which are arranged uniformly spaced and parallel to each, and which are covered with a moisture-insensitive insulating layer, the attainment of the dew point temperature being established by measuring the impedance or capacitance between the two interdigital electrodes. Here, the interdigital electrodes are coated with the moisture-insensitive insulating layer, which completely covers all the free surfaces of the teeth of the interdigital electrodes. The insulating layer consists of a chemically stable, electrically insulating, completely moisture-insensitive material. A suitable metal oxide may also be considered for this purpose. The dew point detection is based on the fact that the total impedance changes when the dew point temperature is reached. This is because condensation droplets begin to form on the sensor surface. A separate condensation droplet layer is therefore formed on the sensor surface, the interdigital electrodes coated with an insulating layer still being present on the sensor surface.

For the functionality of the sensor devices of prior art, it is therefore necessary for the sensor devices to have a plurality of layers, including a condensation core layer.

In principle, a hydrophilic surface is used for the effective change of signal of the sensor.

SUMMARY

On the basis of the evaluation of the state of the art indicated, the object of this invention is to design a sensor device of the type already mentioned in such a manner that there is no separate condensation core layer and the resistance layer simultaneously acts as a condensation core layer.

This object is achieved by a sensor device and a method with the features indicated in claims 1 and 12 respectively.

An advantageous design and suitable further developments of this invention are characterised in the dependent claims.

The resistance layer which is formed by a structuring process to produce two electrodes interdigitally engaging in one another also forms the sensitive layer in the sensor device according to the invention.

However, the core concept of the invention is that the structuring of the interdigital electrodes takes place at the same time as the formation of a moisture-sensitive hydrophilic surface of the same by means of a bundled laser beam.

By selecting suitable laser processing parameters, an action of the laser radiation extending as far as the substrate is produced. The resistance and substrate evaporated in this process is precipitated onto the interdigital electrodes and acts as a condensation core layer on the surface without a closed layer fully forming. The local evaporation of the resistance and substrate results, in ambient atmosphere, in oxidation of the material precipitating as terms on the surface of the interdigital electrodes and in the intervening spaces. In a particularly simple and unique manner, this results in hydrophilisation of the surface, which acts as a condensation core layer. Expensive production plants, comparable to the vacuum plants in laser ablation, are not therefore necessary. In a subsequent sintering process, this surface, provided with cores, is mechanically stabilised.

The combined sensor and electrode layer is present as a corrosion-stable layer which requires no further protective layer or condensation core layer. Since no cover layer is applied to the sensor layer either, in contrast to sensors of prior art, the sensor device according to the invention measures very quickly. Typical detection times for thawing are below 500 ms. Moreover, a sensitivity of the relative humidity in the value range above 90%, and in particular 95%, that is significantly higher than the state of the art, is achieved due to the simplified arrangement.

Compared to the state of the art represented, the sensor device according to the invention therefore has a greatly simplified, hence low cost construction which embodies the advantages of a separate germination layer and hence, in particular, allows a high signal travel within short detection times.

The moisture-sensitive hydrophilic surfaces result in an increase in the dew point temperature on the surface due to a reduction in seam pressure. Thawing therefore takes place and no ambient climate (dew point temperature and relative humidity) is required. The adsorption of water molecules on the surface of the sensor is used as a measuring effect of the sensor device.

In this case, a variation in capacitance of the electrode structure is firstly effected by the variation in dielectricity, and secondly, a resistance variation is effected by a variation in the conductivity of the absorbed water due to ion conduction and the Grothus mechanism.

The structure of the sensor according to the invention provides a resistance layer to be structured on a substrate. Metal oxide layers may be advantageously used as the resistance layer, preferably those formed from ruthenium oxides, ruthenates or iridium oxides.

Typical materials known to the person skilled in the art may be used as substrates, for example circuit board materials, ceramics, glasses or polymers in the form of plates or films.

Two contact electrodes, which are connected to the interdigital electrodes, are preferably installed on the substrate.

The contact electrodes preferably comprise a metal coating and a further layer that can be soldered, bonded or contacted with conducting adhesive.

The invention also allows much cheaper production of a thawing sensor in SMD technology. In this technology surface mountable components (e.g. resistors or capacitors) are applied directly to a circuit board by means of connection surfaces that can be soldered or glued. A standard ceramic substrate may here be used as the substrate. The sensor device according to the invention is suitable for the automated SMD fitting on circuit boards.

If this protective layer is removed there is simultaneously an advantageous detachment of the loose, non-adhering material on the sensor surface so that the remaining core-forming layer produced by the laser process has a particular mechanical long-term stability.

The invention also provides a method for producing a sensor device with a substrate which is preferably formed from an aluminium oxide ceramic, where the formation of a moisture-sensitive hydrophilic surface on the interdigital electrodes and on the recesses is simultaneously associated with the production of interdigital electrodes, the condensation cores being applied to the interdigital electrodes and recesses.

The method comprises in this case of the following method steps:
a) application of contact electrodes to the substrate;
b) application of a resistance layer to the substrate;
c) production of interdigital electrodes from the resistance layer by heating, melting and evaporating parts of the substrate and resistance layer by means of laser radiation;
d) condensation of parts of the evaporated substrate and parts of the evaporated resistance layer on the interdigital electrodes and in the recesses which are provided between the interdigital electrodes;
e) mechanical stabilisation of the condensation cores on the interdigital electrodes and/or in the recesses by sintering.

Within the framework of the method according to the invention the interdigital electrodes may, as described, be formed from a metal oxide layer. In this case it is appropriate for the laser radiation has a wavelength from 248 nm to 1200 nm.

This not completely closed condensation core layer is mechanically stabilised in a sinter process. The sinter parameters are selected here so that condensation particles of a certain grain size are preferably sintered together. In a further preferred embodiment of the invention unsintered condensation cores are removed.

Moreover, the method, in SMD technology, provides for the application of a protective lacquer and the application of the terminal electrodes that can be soldered, for example by means of galvanic separation, or terminal electrodes that can be glued, followed by detachment of the protective lacquer and simultaneous removal of the condensation cores not sintered on.

To ensure that the comb-like sensitive structure, which manifests itself in the interdigital electrodes and in the recesses produced by the laser radiation, in the resistance layer or in the substrate, is not also coated, it must be covered by suitable protective layers before production of the terminal electrodes, which layers can be removed again after the process.

BRIEF DESCRIPTION OF THE DRAWINGS

The invention is explained in greater detail in the following with reference to FIGS. 1 and 2. In diagrammatic representations.

DETAILED DESCRIPTION OF THE PREFERRED EMBODIMENTS

Figure 1:
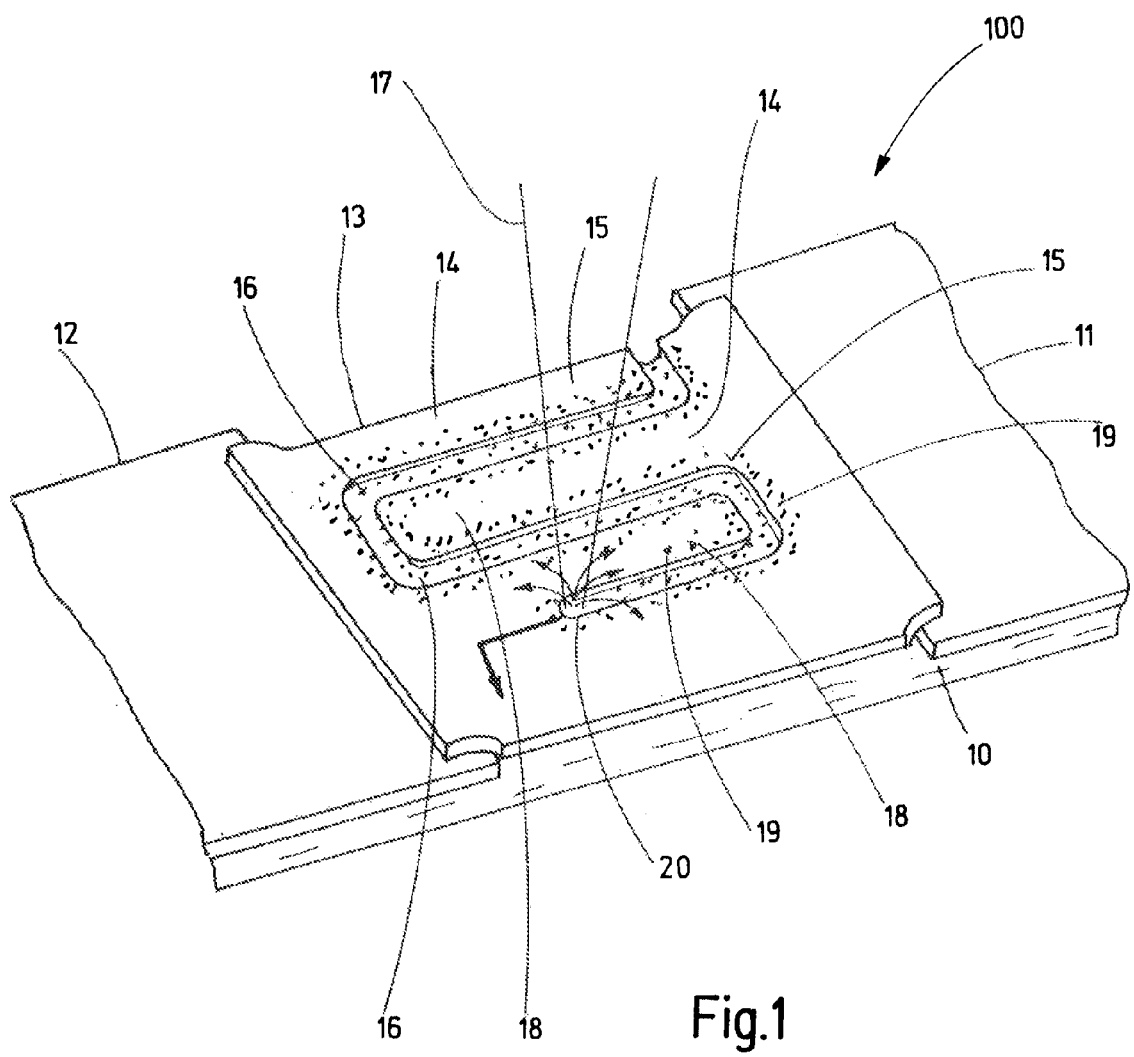
FIG. 1 shows an elevation of a sensor device according to the invention, interdigital electrodes being produced by means of a laser beam on a resistance layer.

FIG. 1 shows a sensor device according to the invention, denoted by reference number 100.

Sensor device 100 has a substrate 10. Substrate 10 may be an aluminium oxide substrate. Moreover, contact electrodes 11, 12 are applied to substrate 10. As can also be seen in FIG. 1, a resistance layer 13 is also arranged on substrate 10, preferably a metal oxide layer. Both contact electrodes 11, 12 and the metal oxide layer can be applied by a screen printing process, then burnt in at suitable temperatures.

Sensor device 100 has interdigital electrodes 14 which are produced in the metal oxide layer by means of laser radiation 17. Resistance layer 13, which is formed by this structure production process to form the interdigital electrodes, is a sensitive layer which, according to the invention, becomes a moisture-sensitive surface due to the introduction of condensation cores 19. Interdigital electrodes 14 are not fully represented, however, in the embodiment shown in FIG. 1. Interdigital electrodes 14 have, in principle, the shape of combs pushed into each other, where the parallel running teeth 15 of interdigital electrodes 14 are separated from one another by furrow-like recesses 16 which are produced by a bundled laser beam 17. Interdigital electrodes 14 are connected to contact electrodes 11, 12 in order to be able to apply a voltage. Furrow-like recesses 16 project through resistance layer 13 into substrate 10. Interdigital electrodes 14 and recesses 16 have a moisture-sensitive hydrophilic surface 18 which contains sintered on condensation cores 19. The local evaporation of material of resistance layer 13 and substrate 10 by laser beam 17 results, in the ambient atmosphere, in oxidation of the material precipitated as condensation cores 19 on interdigital electrodes 14. In a particularly simple, unique manner, this gives rise to hydrophilisation of the surface of interdigital electrodes 14. Condensation cores 19 are conveyed to the surface of interdigital electrodes 14 by means of laser radiation 17, which affects the heating, melting and evaporation of parts of resistance layer 13 and substrate 10. This process is identified in FIG. 1 by reference number 20. As can be seen from FIG. 1, the density of condensation cores 19 on the surface of interdigital electrodes 14 increases in the direction of recesses 16.

Figure 2:
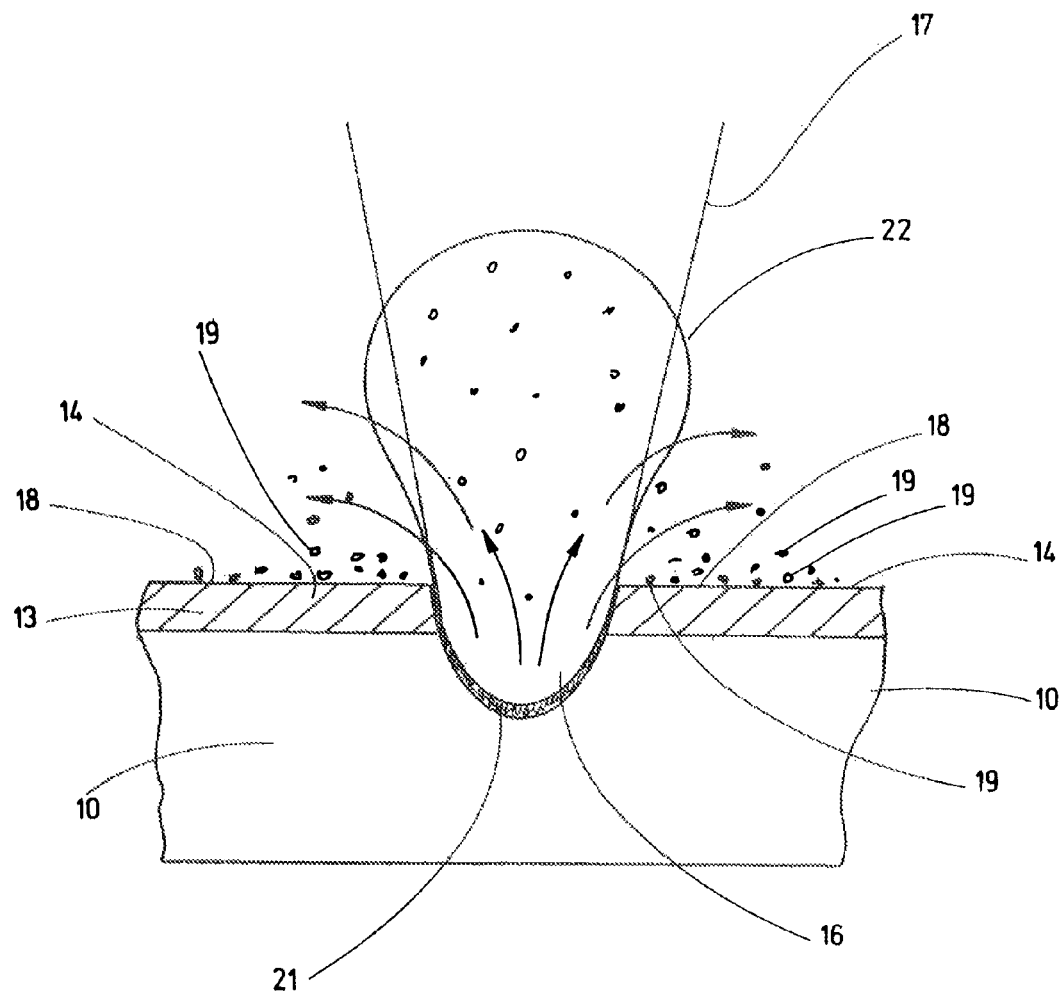
FIG. 2 shows a cross-section through the sensor device in FIG. 1.

The process of the formation of a moisture-sensitive hydrophilic surface with condensation cores 19 that are applied or introduced is explained once again with reference to FIG. 2. In the embodiment shown in FIG. 2, an aluminium oxide substrate also serves as substrate 10, to which contact electrodes 11, 12 and, as a resistance layer 13, a metal oxide layer are also applied here, by means of a screen printing process, for example, then burnt in at suitable temperatures. Interdigital electrodes 14 are produced by the bundled laser beam 17, preferably at a wavelength of approx. 532 nm, or in the region of 1064 nm, in resistance layer 13. Laser beam 17 produces recess 16, which projects through resistance layer 13 into substrate 10. The action of laser radiation 17, which extends into substrate 10 effects heating, melting and evaporation both of parts of resistance layer 13 and parts of substrate 10. This in turn results in the formation of a reaction zone 21 in the form of a melting zone. Material vapour 22 thus produced escapes from recess 16 and is precipitated on interdigital electrodes 14 and recesses 16 in the form of condensation cores 19, so that the surface of interdigital electrodes 14 is present in the form of a moisture-sensitive hydrophilic surface which acts as a condensation core layer, but without the formation of a separate layer. In a subsequent sintering process condensation cores 19 are stabilised by sintering condensation cores 19 on the surface of the interdigital electrodes and the intervening spaces. A moisture-sensitive hydrophilic surface 18, which has the function of a mechanically stabilised condensation core layer, has therefore been formed on sensor device 100. The sintering parameters are selected here so that condensation cores 19 are preferably sintered together to a certain grain size. The remaining condensation cores, not sintered, are removed with a galvanic protection layer after galvanisation.

LIST OF REFERENCE NUMBERS

- 100 Sensor device
- 10 Substrate
- 11 Contact electrodes
- 12 Contact electrodes
- 13 Resistance layer
- 14 Interdigital electrodes
- 15 Teeth
- 16 Recesses
- 17 Laser beam
- 18 Moisture-sensitive hydrophilic surface/condensation core layer
- 18 Condensation cores
- 20 Process
- 21 Reaction zone
- 22 Material vapour

What is claimed is:

1. A sensor device including a resistance layer arranged on a substrate, the sensor device having a moisture-sensitive hydrophilic surface, the sensor device comprising a plurality of interdigital electrodes with recesses formed between the interdigital electrodes, the surface comprising thaw-detecting condensation cores sintered onto the interdigital electrodes and the recesses, wherein the recesses extend through at least a portion of the resistive layer and at least a portion of the substrate.

2. The sensor device according to claim 1, wherein the condensation cores comprise evaporated parts of the resistance layer and parts of the substrate.

3. The sensor device according to claim 1, wherein, if any condensation cores are not sintered onto the surface, non sintered-on condensation cores are removed.

4. The sensor device according to claim 1, wherein the recesses are produced by laser beams, wherein the density of the condensation cores on the interdigital electrodes increases in the direction of the recesses.

5. The sensor device according to claim 1, wherein the interdigital electrodes are formed in a resistance layer of a substrate of the sensor device.

6. The sensor device according to claim 5, wherein the substrate is one of aluminium oxide, circuit board material, glass, or glass ceramic.

7. The sensor device according to claim 5, wherein two terminal contacts are applied to the substrate, and wherein the contacts are connected to interdigital electrodes.

8. The sensor device according to claim 5, wherein the resistance layer comprises a metal oxide layer.

9. The sensor device according to claim 8, wherein the metal oxide layer comprises ruthenium oxides, ruthenates, or iridium oxides.

10. The sensor device according to claim 8, wherein the metal oxide layer is a metal oxide paste.

11. A method for forming a moisture-sensitive hydrophilic surface on a sensor device having a resistive layer arranged on a substrate, the sensor device comprising a plurality of interdigital electrodes with recesses formed between the interdigital electrodes, the method comprising sintering thaw-detecting condensation cores onto the interdigital electrodes and the recesses, wherein the recesses extend through at least a portion of the resistive layer and at least a portion of the substrate.

12. The method according to claim 11, wherein the method is not carried out in a vacuum.

13. The method according to claim 11, wherein the recesses are formed by the application of laser radiation.

14. The method according to claim 13, wherein laser radiation is carried out at a wavelength from 248 nm to 1200 nm.

15. The method according to claim 11, wherein the interdigital electrodes are formed in the resistance layer.

16. The method according to claim 15, wherein the substrate is formed from an aluminium oxide ceramic.

17. The method according to claim 15, further comprising applying contact electrodes to the substrate.

18. The method according to claim 15, wherein the interdigital electrodes are formed in the resistance layer by heating, melting and evaporating parts of the substrate and resistance layer by laser radiation.

19. The method according to claim 15, wherein a reaction zone, in which heating, melting and evaporation of the substrate and the resistance layer takes place, is formed by laser radiation.

20. The method according to claim 15, wherein the interdigital electrodes are formed from a metal oxide layer.

21. The method according to claim 20, wherein the metal oxide layer comprises ruthenium oxide, ruthenates, or iridium oxides.

* * * * *